(12) United States Patent
Heimer

(10) Patent No.: US 6,212,015 B1
(45) Date of Patent: *Apr. 3, 2001

(54) ROD LENSES

(75) Inventor: Richard J. Heimer, Los Angeles, CA (US)

(73) Assignee: Radiant Optics, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/413,453

(22) Filed: Oct. 6, 1999

(51) Int. Cl.$^7$ .................................................. G02B 1/06
(52) U.S. Cl. ................................. 359/665; 359/797
(58) Field of Search ............................ 359/665, 660, 359/797

(56) References Cited

U.S. PATENT DOCUMENTS

| | | | |
|---|---|---|---|
| 2,171,640 | 9/1939 | Berek | 359/778 |
| 3,257,902 | 6/1966 | Hopkins | 359/435 |
| 3,364,816 | 1/1968 | Jeffree | 359/795 |
| 3,799,656 | 3/1974 | Fleischman | 359/777 |
| 4,168,882 | 9/1979 | Hopkins | 359/665 |
| 5,892,625 | 4/1999 | Heimer | 359/665 |

Primary Examiner—Scott J. Sugarman
Assistant Examiner—Evelyn A. Lester
(74) Attorney, Agent, or Firm—Rockey, Milnamow & Katz, Ltd.

(57) ABSTRACT

A rod lens comprises a sleeve having two opposite ends, two correcting lenses, one at each of the opposite ends of the sleeve, and a light-transmitting fluid contained within an enclosed space defined by the sleeve and by the correcting lenses. The correcting lens at one of the opposite ends of the sleeve is non-convex. The correcting lens at the other end of the sleeve is convex. Depending upon what properties are sought, the non-convex lens may be planar or concave, and the light-transmitting fluid may exhibit optical properties of flint glass or of crown glass. If a liquid, the light-transmitting fluid may be water or a non-aqueous liquid.

12 Claims, 2 Drawing Sheets

ROD LENSES

TECHNICAL FIELD OF THE INVENTION

This invention pertains to rod lenses of a type comprising a sleeve, a correcting lens at each end of the sleeve, and a contained fluid. Such rod lenses are useful, as relay lenses, in medical or technical endoscopes.

BACKGROUND OF THE INVENTION

Rod lenses of the type noted above are disclosed in U.S. Pat. No. 5,892,625, the disclosure of which is incorporated herein by reference. Rod lenses according to this invention are similar in certain respects to but differ in other respects from rod lenses disclosed in U.S. Pat. No. 5,892,625.

Reference is made to the description of the prior art in U.S. Pat. No. 5,892,625, from column 1, line 16, through column 2, line 61, and to the several references cited on its title page, namely U.S. Pat. No. 2,171,640, U.S. Pat. No. 3,257,902, U.S. Pat. No. 3,364,816, U.S. Pat. No. 3,799,656, and U.S. Pat. No. 4,168,882. Reference is made to the description of optical glasses and optical liquids in U.S. Pat. No. 5,892,625, in column 5, lines 1 through 57.

SUMMARY OF THE INVENTION

This invention provides a rod lens of the type noted above, which is durable, inexpensive, and energy efficient, and which can be advantageously used in a medical or technical endoscope. The rod lens comprises a sleeve having a correcting lens at each of its opposite ends and a containing a light-transmitting fluid.

The correcting lens at one of the opposite ends of the sleeve is convex and the correcting lens at the other end of the sleeve is non-convex. If the non-convex lens is planar, the rod lens may be then characterized as plano-convex, which is preferred, or as convexo-planar. If the non-convex lens is concave, the rod lens may be then characterized as concavo-convex, which is preferred, or as convexo-concave.

The light-transmitting fluid may exhibit optical properties of flint glass or of crown glass. Preferably, the light-transmitting fluid is be water, which exhibits optical properties of crown glass, or a non-aqueous liquid. Preferably, whether or not a liquid, the light-transmitting fluid constitutes the sole contents of an enclosed space defined by the sleeve and by the correcting lenses.

Optical properties of the rod lens depend upon whether the rod lens is plano-convex or concavo-convex and upon whether the light-transmitting fluid exhibits optical properties of flint glass or of crown glass.

These and other objects, features, and advantages of this invention are evident from the following description of two contemplated embodiments of this invention, with reference to the accompanying drawings.

DETAILED DESCRIPTION OF THE ILLUSTRATED EMBODIMENTS

U.S. Pat. No. 5,892,625 characterized the construction of biconvex rod-like lenses in terms of the shape and power of their constituent fluid lenses, having examined the biconvex (positive power), bi-concave (negative power), and concavo-convex (positive power) variations. Now, in the preferred embodiments 1 and 2 of the present invention, we describe plano-convex and concavo-convex rod-like lenses containing respectively fluid lenses that are concavo-convex in shape.

Figure 1:
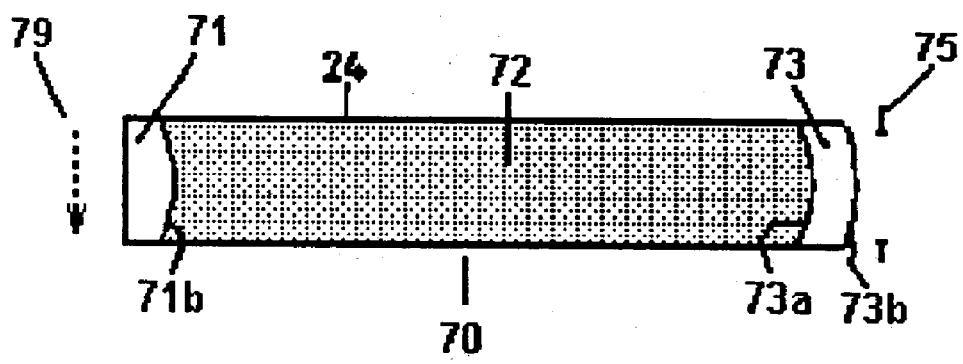
FIG. 1 is a schematic representation of a side view of a rod lens constituting a first embodiment of this invention.

Embodiment 1 of the present invention, the diagrammatic axial section of which is shown in FIG. 1 is a module comprising an axially aligned triplet lens assembly 70. Triplet 70 includes field lens 71, an objective lens 73, said field lens and objective separated by an optical fluid lens 72. Fluid lens 72 is encapsulated by fluid contacting surfaces 71*b* and 73*a* and the thin-walled sleeve 24 previously described. Lens elements 71 and 73 are attached to sleeve 24 by a fastening means to form a liquid-tight seal. Surface 73*b* in a conic surface of revolution and specifically, a prolate spheroid. The configuration of the triplet 70 is defined by object plane 79, a field lens 71, a concavo-convex liquid lens 72 and a pupil plane 75.

An aperture stop is provided at surface 75 to define the aperture of the assembly 70. A field stop is similarly provided at surface 79 to define the diametrical extent of the field of view. Tubular spacers (not shown) conveniently provide the proper spacing of this module to its symmetrical counterpart and to the adjacent image transmitting system in FIG. 1.

The flexible fluid middle portion 72 of the half module 70 of the image transmitting system is a cylindrically shaped element having a positive optical power. Field lens 71 and objective lens 73 are made of polystyrene. The fluid middle portion 72 of the assembly is sterile water.

Figure 2:
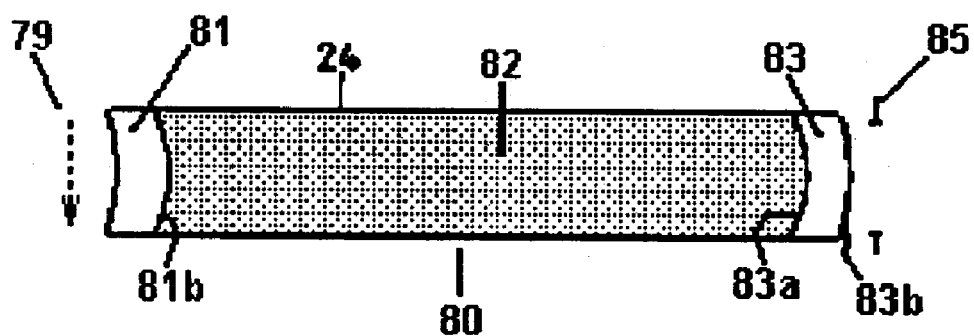
FIG. 2 is a schematic representation of a side view of a rod lens constituting a second embodiment of this invention.

Embodiment 2 of the present invention, the diagrammatic axial section of which is shown in FIG. 2, is an axially aligned triplet assembly 80. Triplet 80 consists of a field lens 81 and an objective lens 83 separated by an optical fluid lens 82 which is encapsulated by fluid contacting surfaces 81*b*, 83*a* and a thin-walled sleeve 24. Surface 83*b* is a conic section of revolution, specifically a prolate spheroid. Field lens 81 and objective lens 83 are fastened to sleeve 24, as described above, to form a liquid-tight seal. The flexible middle portion 82 of the half module 80 of the image transmitting system is a cylindrically shaped element having a positive optical power.

The configuration of triplet 80 is defined by object plane 79, field lens 81, objective lens 83 and pupil plane 85, to respectively define the extent of the field of view and aperture diameter of the assemblage. Tubular spacers (not shown in FIG. 2) provide the proper longitudinal spacing of triplet 80 to its symmetrical counterpart and adjacent image transmitting optical systems.

The refractive materials utilized in half-module triplet 80 of the image transmitting optical system consists of field and objective lenses made of polystyrene and a fluid middle portion made of sterile water.

Materials specified in U.S. Pat. No. 5,892,625 for the correcting lenses of the rod lenses disclosed therein and for the light-transmitting fluids of the rod lenses disclosed therein may also be used in the embodiments of the present invention. The light-transmitting fluid may have optical properties of flint glass or of crown glass. The light-transmitting fluid may be water, which has optical properties of crown glass, or a non-aqueous liquid.

The following equations describe the numerical data for Embodiments 1 and 2 of the present invention, presented in Tables 1 and 2. The radius of a given surface of adjacent surfaces i and j will be designated $t_{ij}$, the index of refraction and Abbe number of the material medium between given surfaces i and j will be designated $N_{ij}$ and $v_{ij}$ respectively. All dimensions are reported in millimeters. The aspherical surfaces of Embodiments 1 and 2 are defined by the expression disclosed in U.S. Pat. No. 5,892,625 is utilized.

TABLE 1

Embodiment 1

$NA_0^1 = 0.53$     $O.D.^2 = 2$     ½ track³ = 31.8

| Object | | air | |
|---|---|---|---|
| $R_1 = 12.267$ | $T_{0,1} = 2.122$ | | |
| $R_2 = 3.185$ | $T_{1,2} = 1.000$ | $N_{1,2} = 1.59501$ | $v_{1,2} = 30.62$ |
| $R_3 = 5.161$ | $T_{2,3} = 27.558$ | $N_{2,3} = 1.33447$ | $v_{2,3} = 56.0$ |
| $R_4 = 6.807$ | $T_{3,4} = 1.000$ | $N_{3,4} = 1.59501$ | $v_{3,4} = 30.62$ |
| | $T_{4,5} = 0.100$ | air | $k_4 = 0.13957$ |

Aperture Stop
[1] = numerical aperture, the sine of the ½ angle that object ray makes with the axis, defines system speed
[2] = object diameter
[3] = distance between object and stop plane

TABLE 2

Embodiment 2

$NA_0^1 = 0.53$     $O.D.^2 = 2$     ½ track³ = 31.8

| Object | | air | |
|---|---|---|---|
| $R_1$ = plano | $T_{0,1} = 2.955$ | | |
| $R_2 = 4.789$ | $T_{1,2} = 1.000$ | $N_{1,2} = 1.59501$ | $v_{1,2} = 30.62$ |
| $R_3 = 4.175$ | $T_{2,3} = 24.989$ | $N_{2,3} = 1.33447$ | $v_{2,3} = 56.0$ |
| $R_4 = 5.993$ | $T_{3,4} = 1.000$ | $N_{3,4} = 1.59501$ | $v_{3,4} = 30.62$ |
| | $T_{4,5} = 0.100$ | air | $k_4 = 0.02296$ |

Figure 3:
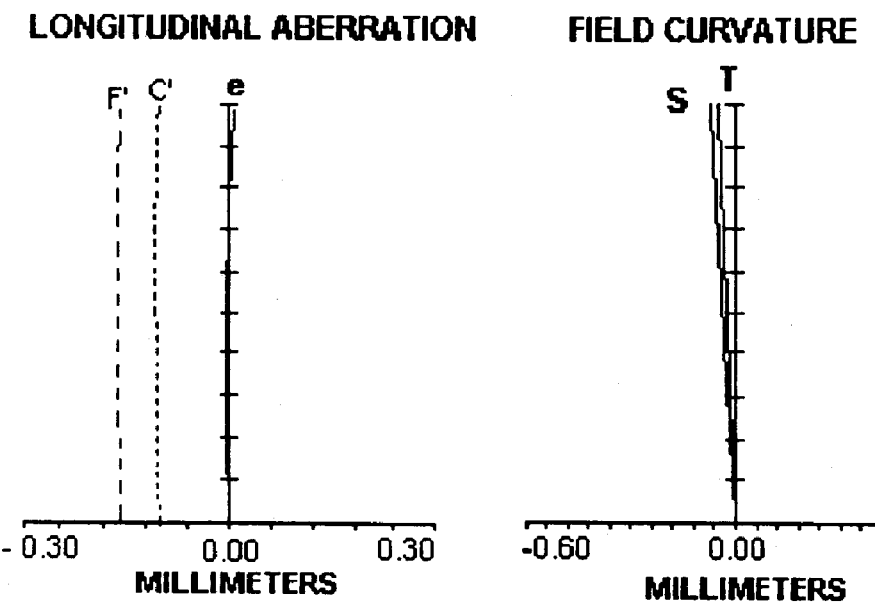
FIG. 3 is a graph of the longitudinal aberration and the astigmatic field curves of the first embodiment of this invention.
Figure 4:
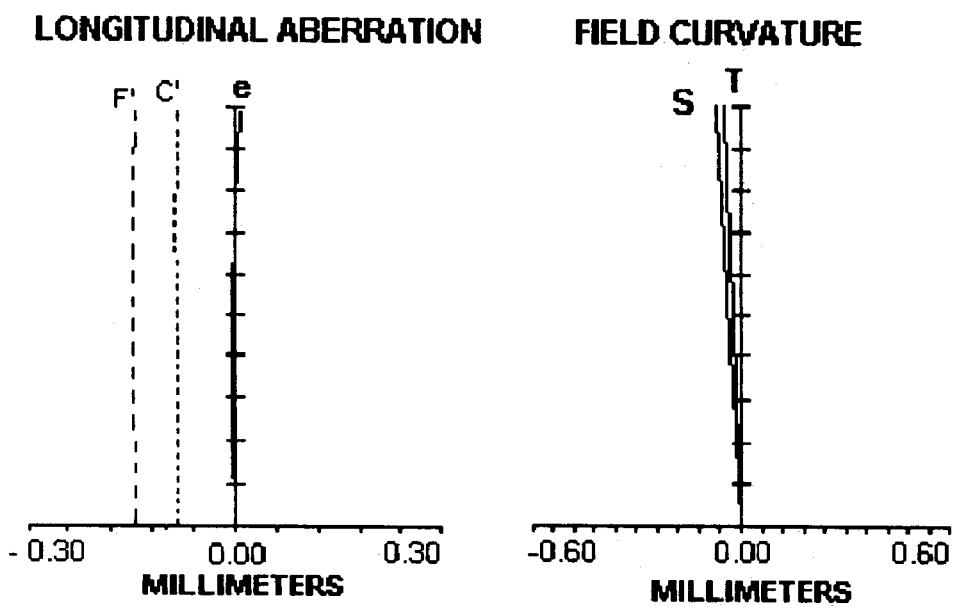
FIG. 4 is a graph of the longitudinal aberration and the astigmatic field curves of the second embodiment of this invention.

Aperture Stop
[1] = numerical aperture, the sine of the ½ angle that object ray makes with the axis, defines system speed
[2] = object diameter
[3] = distance between object and stop plane The aberration characteristics of Embodiment 1 when arranged in a symmetrical opposing pair of modules about a common aperture stop is shown in FIG. 3. Similarly, the aberration characteristics of Embodiment 2, when paired with its inverted common module, is shown in FIG. 4. In FIGS. 3 and 4, the characteristics shown are longitudinal aberration and astigmatic field curve plots (for both the tangential (T) and the sagittal (S) azimuth) as a function, respectively, of relative normalized pupil radius and relative normalized image height, the former shown at three wavelengths, e (546.1-nm), C' (643.8-nm) and F' (480-nm).

In summary, it can be seen that the present invention, in which two contrasting configuration solutions of a rod-like fluid encapsulated rod-like lens has been presented. Said lens modules eliminate the need for multiple glass element cemented assemblies in image transmitting optical systems.

In both Embodiments of the present invention, the rod-like lens simply consists of two lens elements and a fluid therebetween.

The features of the present invention include:

1) insensitivity to glass fracture or breakage when shear and compressive forces are applied;
2) economy in manufacture and assembly; and
3) residual values of composite image errors, which are generally, less than other prior art image transmitting optical systems.

While the above description contains many specificities, these should not be construed as limitations on the scope of the invention, but rather as exemplification of the preferred embodiments thereof. Many other variations are possible, for example, the means of encapsulation, the use of aspheric surfaces other than conics, and the choice of refractive materials among others. Accordingly, the scope of the invention should be determined not by the Embodiments illustrated, but by the appended claims, or their equivalents.

Various modifications may be made in either embodiment described above without departing from the scope and spirit of this invention.

I claim:

1. A rod lens comprising a sleeve having two opposite ends, two correcting lenses, one at each of the opposite ends of the sleeve, and a light-transmitting fluid contained within an enclosed space defined by the sleeve and by the correcting lenses, wherein the correcting lens at one of the opposite ends of the sleeve is non-convex, and wherein the correcting lens at the other end of the sleeve is convex.

2. The rod lens of claim 1 wherein the non-convex lens is a planar lens.

3. The rod lens of claim 1 wherein the non-convex lens is a concave lens.

4. The rod lens of claim 1, 2, or 3 wherein the light-transmitting fluid exhibits optical properties of flint glass.

5. The rod lens of claim 1, 2, or 3 wherein the light-transmitting fluid exhibits optical properties of crown glass.

6. The rod lens of claim 1, 2, or 3 wherein the light-transmitting fluid is water.

7. The rod lens of claim 1, 2, or 3 wherein the light-transmitting fluid is a non-aqueous liquid.

8. The rod lens of claim 1, 2, or 3 wherein the light-transmitting fluid constitutes essentially the sole contents of an enclosed space defined by the sleeve and by the correcting lenses.

9. The rod lens of claim 8 wherein the light-transmitting fluid exhibits optical properties of flint glass.

10. The rod lens of claim 8 wherein the light-transmitting fluid exhibits optical properties of crown glass.

11. The rod lens of claim 8 wherein the light-transmitting fluid is water.

12. The rod lens of claim 8 wherein the light-transmitting fluid is a non-aqueous liquid.

* * * * *